April 3, 1934. F. SPANBAUER Plant Pat. 91
RED ROSE
Filed Nov. 6, 1933
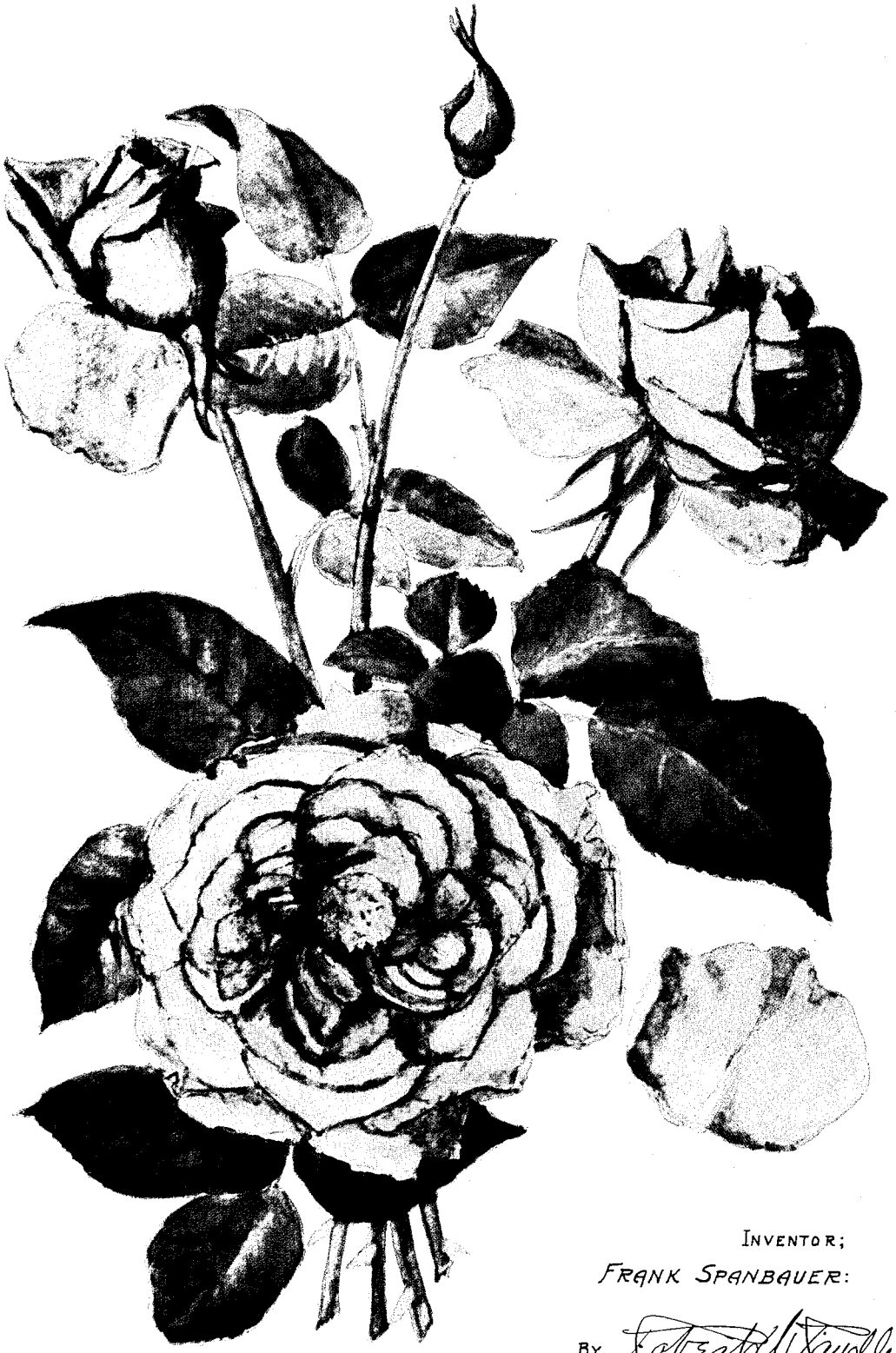
INVENTOR;
FRANK SPANBAUER:
BY Robert B. Rawlle,
ATTORNEY.

Patented Apr. 3, 1934

Plant Pat. 91

UNITED STATES PATENT OFFICE

91

RED ROSE

Frank Spanbauer, Medina, N. Y.

Application November 6, 1933, Serial No. 696,814

1 Claim. (Cl. 47—61)

This application relates to the production of a new variety of rose, the same being unique in its general character, and majestic in appearance, having colors which are attractive to one's sight and which are practically changeless throughout its entire blooming period, and producing an aroma which is sweet scented, voluminous, and penetrating in character.

The accompanying illustration, forming a part of this specification, displays my rose in various stages of development, and also the shape, color, and various other features thereof, as near as can be done artificially; and also showing a detail view of one of the inner petals, which view is especially for the purpose of visualizing the small white streak at the base of its petal, which is hereinafter referred to.

As to the various features of my rose, herein described, due allowance should be given for differences in soil, the amount of sunshine and shade, the humidity of the surrounding atmosphere, and the attention which may be given thereto.

This rose was secured by hybridization in September 1930, in which "My Lady rose", a dark red hybrid tea rose, was employed as the male member, and the "Matchless", a deep cerise hybrid tea rose, as female member. From the stamens of the male member pollen was taken and placed in the stigmas of the female member, causing the female member to produce seeds which in due course of time ripened and dried. Said seeds were produced near Kansas City, Missouri.

Early in April 1931 I planted said seeds in proper soil, at Medina, in the State of New York, but only one of them proved to be viable, but this one grew and brought forth a plant which I grafted onto a root of a wild rose plant, called "Manetti", which eventuated in the production of my new rose in December, 1931. From said plant I grafted and budded eleven plants, in the spring of 1932, which I planted under glass. During the winter of 1932–33 I grafted from the eleven plants above mentioned, and they produced two-thousand plants, most of which are now maturing at Medina, in the State of New York, and others in the greenhouses of the Joseph H. Hill Company at Richmond, Indiana. The first of those planted at Medina, New York, are now in marketable condition, as those shown in the accompanying illustration which was made directly from those grown at Medina, New York. This plant, including its bloom, has not been introduced to the public prior to May 23, 1930.

All of the plants and their bloom thus far produced and being produced are exactly like the original single plant in every particular, therefore it is believed that the characteristics thereof, which are herein described and claimed, have become permanently fixed as a new variety.

*The peduncles,* or main stems of my new rose, are long, straight, erect and stiff, and they are light green in color, each producing a great number of short downwardly and outwardly projecting V-shaped spines, which are of a still lighter shade of green than that of the peduncles with which they are connected.

Projecting upwardly from each of said peduncles is a large number of leaf-branches, or twigs of a green color, which are also provided with V-shaped spines. Said leaf branches carry a large number of compound leaves, as is hereinafter set forth.

*The foliage* in this instance is very abundant, and it is of an attractive appearance, both as to shape and color. Protruding from each of the leaf branches or rachises are a plurality of petioles or very short leaf-branches, each of which carries a single leaf. Each of said leaves is ovate in contour, each terminating at its outer end in a sharp point, and the periphery of each leaf is minutely serrated throughout. The obverse side of each leaf is velvety and is of an extremely dark green color, while the reverse side of each leaf is of an unusually light shade of green, and each leaf is leathery in its texture.

*Aroma.*—One of the noticeable features of my new rose resides in its voluminous exuberance of a delectable aroma or fragance, which includes a "Wild rose" fragrance.

*Reproduction.*—My new rose is self polleniz-ing, and it is very prolific in its reproduction. The stamens are comparatively large, and are pale white in color, as are also the anthers containing the pollen. The ovaries, containing the seed, are of a pale yellowish color. The seeds are of medium size, and their color fluctuates throughout the season, depending upon the status of development. The styles are long, and are of a yellowish cast in color. The filaments are of medium size, and are yellowish in color, but they are hardly perceptible to the naked eye.

Said parts, perhaps, would have no particular relation to a description of my rose, but for the fact that collectively they form the central portion, and give to it a distinctive yellow color, which adds materially to the beauty of the bloom by reason of the contrast with the deep red color of the petals.

*The bloom.*—The petals of my new rose are of a very deep, glowing, vivid dark red color, especially throughout their outer half, and to a great extent throughout the inner half thereof, and there is no apparent change in the color throughout their entire period of existence, except that as they near the point of dissolution they become pink in color.

The petals have a fine velvety texture throughout their period of existence, the same being apparent on both sides of the petals.

There is no perceptible difference of the color between the obverse and the reverse exposure of the petals, except when the bloom is fully open there will be found a narrow white streak at the central base portion thereof, but this seldom occurs with other than the inner petals.

The general shape of the petals is substantially orbiculate.

The petals are usually slightly crinkled around their peripheral portions; and their outer portions are inclined to turn downwardly at an angle from that of the main portion thereof, but this seldom occurs except with relation to the outer petals.

The bloom are profuse, and are always borne singly.

Each of the bloom has an average of forty-two petals in winter, and thirty-eight in summer, varying some what according to climatic conditions and the amount of proper attention devoted thereto.

The calyx is composed of a plurality of pointed sepals.

The bloom, when fully opened, measures an average of four and one-half inches in diameter.

A novel characteristic of the bloom is that there are approximately twenty large petals forming the outer part of the bloom, from which they decrease in size to the corona, and the inner petals form themselves in the shape of a star, the same being more apparent during the summer and early fall.

The inner half of each bloom appears to be double, while the outer half appears to be single.

*Miscellaneous features.*—My rose is known as "continuous blooming".

My rose is very vigorous in its growth, and withstands medium cold weather without injury thereto, and it is classified as free blooming.

The buds are ovate in shape while inclosed by the calyx.

My rose plant is classed as a bush, and it grows tall and compact and produces approximately twenty-eight bloom to each plant, within a period of twelve months.

I have not allowed this variety of rose to produce fruit, as I remove the old bloom before fruit has developed.

Having now fully shown and described my new rose plant, what I claim and desire to secure by Letters Patent, is—

A new and distinct variety of rose plant, substantially as herein described, which is particularly characterized by the very deep glowing red color of its petals and the velvety texture thereof throughout the normal visible extent both as to the obverse and reverse exposure thereof; its extremely vigorous growth; the practically round shape of its petals; the fact that the outer petals appear single while the inner petals appear as double in each bloom; the fact that the inner petals are normally so arranged that they appear in the shape of a star; the very prominent regenerating organs, which are of a yellowish color thereby causing the central portion of the fully opened bloom to contrast with relation to the petals; its voluminous exuberance of a delectable and penetrating aroma; and its beauty of color, shape, and appearance as an entirety.

FRANK SPANBAUER.